United States Patent
Mande et al.

(10) Patent No.: US 9,372,959 B2
(45) Date of Patent: Jun. 21, 2016

(54) ASSEMBLY OF METAGENOMIC SEQUENCES

(75) Inventors: Sharmila Shekhar Mande, Hyderabad (IN); Tarini Shankar Ghosh, Hyderabad (IN); Varun Mehra, Hyderabad (IN)

(73) Assignee: Tata Consultancy Services Limited, Mumbai, Maharashtra (IN)

( * ) Notice: Subject to any disclaimer, the term of this patent is extended or adjusted under 35 U.S.C. 154(b) by 351 days.

(21) Appl. No.: 13/484,885

(22) Filed: May 31, 2012

(65) Prior Publication Data
US 2013/0325428 A1 Dec. 5, 2013

(30) Foreign Application Priority Data

Feb. 10, 2012 (IN) .............................. 388/MUM/2012

(51) Int. Cl.
*G06F 19/24* (2011.01)
*G06F 19/22* (2011.01)

(52) U.S. Cl.
CPC ................ *G06F 19/24* (2013.01); *G06F 19/22* (2013.01)

(58) Field of Classification Search
None
See application file for complete search history.

(56) References Cited

PUBLICATIONS

Caro-Quintero, A. et al. Unprecedented levels of horizontal gene transfer among spatially co-occurring Shewanella bacteria from the Baltic Sea. ISME J. 5, 131-40 (2011).*
Kristiansson, E. et al. Pyrosequencing of antibiotic-contaminated river sediments reveals high levels of resistance and gene transfer elements. PLoS One 6, e17038 (2011).*
Kurokawa, K. et al. Comparative metagenomics revealed commonly enriched gene sets in human gut microbiomes. DNA Res. 14, 169-181 (2007).*
Mavromatis, K. et al. Use of simulated data sets to evaluate the fidelity of metagenomic processing methods. Nat. Methods 4, 495-500 (2007).*
Mrázek, J. Phylogenetic signals in DNA composition: limitations and prospects. Mol. Biol. Evol. 26, 1163-1169 (2009).*
Palenik, B., Ren, Q., Tai, V. & Paulsen, I. T. Coastal Synechococcus metagenome reveals major roles for horizontal gene transfer and plasmids in population diversity. Environ. Microbiol. 11, 349-359 (2009).*
Sandberg, R. et al. Capturing whole-genome characteristics in short sequences using a naïve Bayesian classifier. Genome Res. 11, 1404-1409 (2001).*
Tamames, J. & Moya, A. Estimating the extent of horizontal gene transfer in metagenomic sequences. BMC Genomics 9, 136 (2008).*
Zheng, H. & Wu, H. Short Prokaryotic DNA Fragment Binning Using a Hierarchical Classifier Based on Linear Disciminant Analysis and Principal Component Analysis. J. Bioinform. Comput. Biol. 08, 995-1011 (2010).*

(Continued)

*Primary Examiner* — Soren Harward
(74) *Attorney, Agent, or Firm* — Lee & Hayes, PLLC

(57) ABSTRACT

Systems and methods for assembly of metagenomic sequences are described herein. In one embodiment, a plurality of metagenomic sequences is represented in three dimensional space to obtain a plurality of sequence vectors. Based on plurality of the sequence vectors, a cuboid having a plurality of grids is defined in the three dimensional space such that it encompasses the plurality of metagenomic sequences. Further, the plurality of metagenomic sequences is assembled into one or more contigs based on traversal of the plurality of grids. In one implementation, the one or more contigs are assembled such that a contig includes metagenomic sequences probably originating from the same genome.

7 Claims, 5 Drawing Sheets

(56) References Cited

PUBLICATIONS

Abe, T., Sugawara, H., Kinouchi, M., Kanaya, S. & Ikemura, T. Novel phylogenetic studies of genomic sequence fragments derived from uncultured microbe mixtures in environmental and clinical samples. DNA Research 12, 281-290 (2005).*

Bao, E., Jiang, T., Kaloshian, I. & Girke, T. Seed: efficient clustering of next-generation sequences. Bioinformatics 27, 2502-2509 (2011).*

Chan, C. K. K., Hsu, A. L., Tang, S. L. & Halgamuge, S. K. Using growing self-organising maps to improve the binning process in environmental whole-genome shotgun sequencing. Journal of Biomedicine and Biotechnology 2008, 1-10 (2008).*

Liao, W., Liu, Y. & Choudhary, A. A Grid-based Clustering Algorithm using Adaptive Mesh Refinement. in Seventh Workshop on Mining Scientific and Engineering Datasets in conjunction with the SIAM International Conference on Data Mining (2004).*

Raes, J., Foerstner, K. U. & Bork, P. Get the most out of your metagenome: computational analysis of environmental sequence data. Current Opinion in Microbiology 10, 490-498 (2007).*

Teeling, H., Meyerdierks, A., Bauer, M., Amann, R. & Glöckner, F. O. Application of tetranucleotide frequencies for the assignment of genomic fragments. Environmental Microbiology 6, 938-947 (2004).*

Huang, X. & Madan, A. CAP3: A DNA sequence assembly program. Genome Research 9, 868-877 (1999).*

Kumar, S. & Blaxter, M. L. Comparing de novo assemblers for 454 transcriptome data. BMC Genomics 11, 571 (2010).*

Pignatelli, M. & Moya, A. Evaluating the Fidelity of De Novo Short Read Metagenomic Assembly Using Simulated Data. PLoS One 6, e19984:1-9 (2011).*

Issaac Rajan, Sarang Aravamuthan and Sharmila S. Mande; Identification of compositionally distinct regions in genomes using the centroid method; Bioinformatics; 2007; pp. 2672-2677; vol. 23 No. 20 2007; published by Oxford University Press.

Robersy Sanchez and Ricardo Grau; Vector Space of the Extended Base-triplets over the Galois Field of five DNA Bases Alphabet; International Journal of Biological and Life Sciences; 3:2 2007; pp. 89-96.

* cited by examiner

ASSEMBLY OF METAGENOMIC SEQUENCES

TECHNICAL FIELD

The present subject matter relates, in general, to the field of metagenomics and, in particular, to assembly of sequences constituting metagenomic data.

BACKGROUND

The study of genetic material recovered directly from an environmental sample, by sequencing the genetic material, is referred to as metagenomics. Metagenomics provides information pertaining to taxonomic diversity and physiology of various organisms present in the environmental sample.

A facility, such as a research laboratory or a clinic, involved in genomic study typically uses high capacity platforms, such as next generation sequencing (NGS) platforms, capable of generating huge volumes of metagenomic data every year. The metagenomic data thus generated may be further analyzed, for example, to determine various organisms present in the metagenomic data and to identify the functional roles of the various genes they encompass. Generally, the metagenomic data may be stored for further analysis and future studies. Thus, each year metagenomic data is generated in huge volumes, in the range of hundreds of terabytes (TB), and stored in repositories for future studies.

In order to analyze the metagenomic data, nucleotide sequences, such as DNA or RNA sequences constituting the metagenomic data are generally assembled into larger sequences called contigs. The process of assembly typically involves performing a pairwise comparison of the nucleotide sequences, numbering in millions, thus requiring huge computational resources and infrastructure. Furthermore, an attempt to assemble nucleotide sequences, originating from genomes of a large number of organisms belonging to diverse taxonomic groups, may result in formation of erroneous chimeric sequences, which may affect the results of analyses of the metagenomic data.

SUMMARY

This summary is provided to introduce concepts related to assembly of metagenomic sequences, which are further described below in the detailed description. This summary is not intended to identify essential features of the claimed subject matter nor is it intended for use in determining or limiting the scope of the claimed subject matter.

Method(s) and a system(s) for assembly of metagenomic sequences are described herein. In one implementation, the method for assembly of metagenomic sequences includes representing each of a plurality of metagenomic sequences in three dimensional space to obtain a plurality of sequence vectors. Further, a cuboid having a plurality of equally sized smaller cuboids, hereinafter referred to as grids is defined in the three dimensional space based on the plurality of sequence vectors. In one implementation, the cuboid is defined such that it encompasses sequence vectors corresponding to the plurality of metagenomic sequences. Furthermore, the plurality of grids is progressively traversed to identify and assemble the plurality of metagenomic sequences into one or more contigs. In one implementation, the one or more contigs are assembled such that a contig includes metagenomic sequences probably originating from the same genome.

BRIEF DESCRIPTION OF THE DRAWINGS

The detailed description is described with reference to the accompanying figures. In the figures, the left-most digit(s) of a reference number identifies the figure in which the reference number first appears. The same numbers are used throughout the drawings for reference to like features and components.

DETAILED DESCRIPTION

Figure 1:
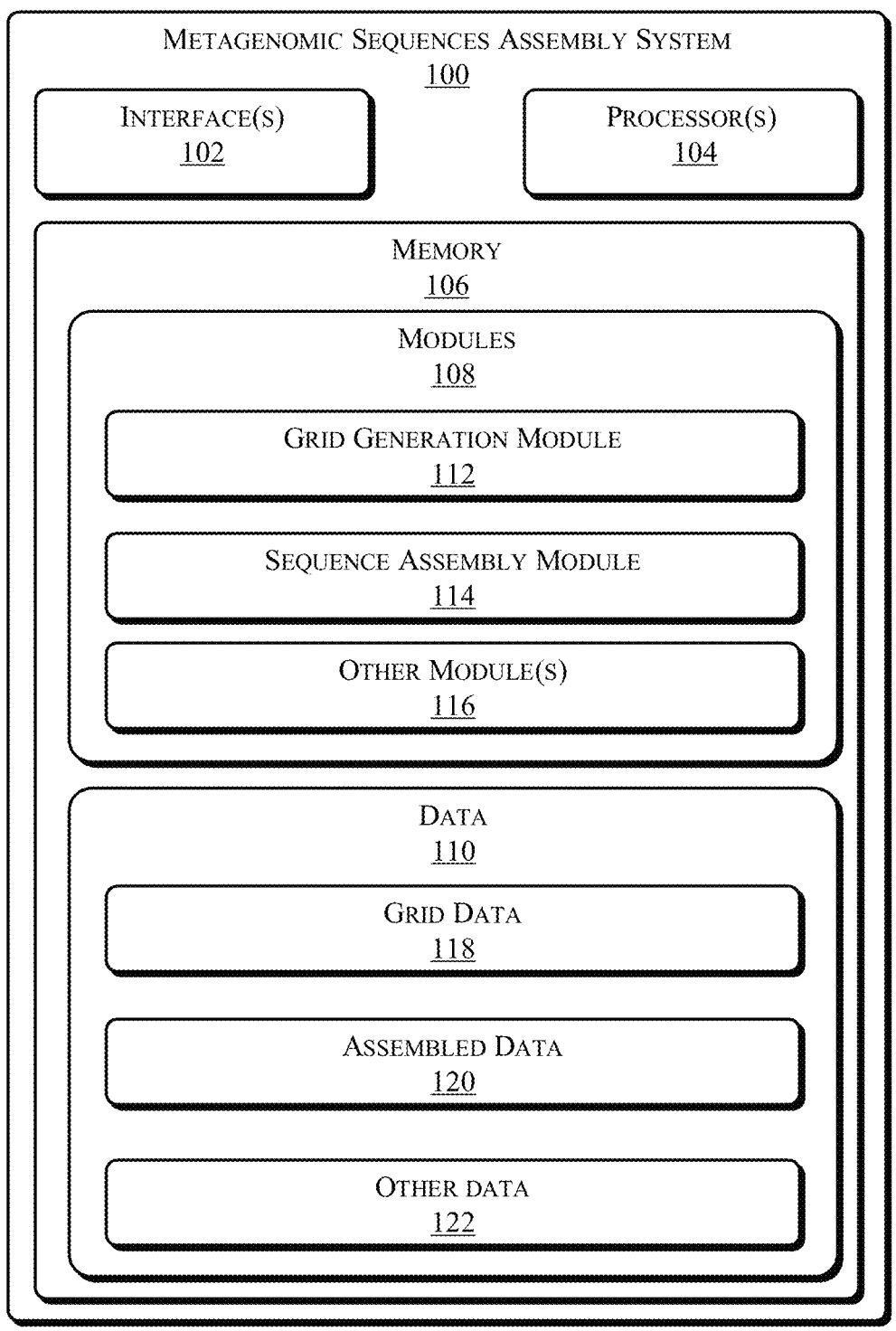
FIG. 1(a) illustrates a metagenomic sequences assembly system, in accordance with an embodiment of the present subject matter.
FIG. 1(b) illustrates a cuboid generated by the metagenomic sequences assembly system for assembly of metagenomic sequences, in accordance with an embodiment of the present subject matter.
FIG. 1(c) illustrates a pictorial representation of progressive traversal performed on the cuboid by the metagenomic sequences assembly system, in accordance with an embodiment of the present subject matter.
Figure 1:
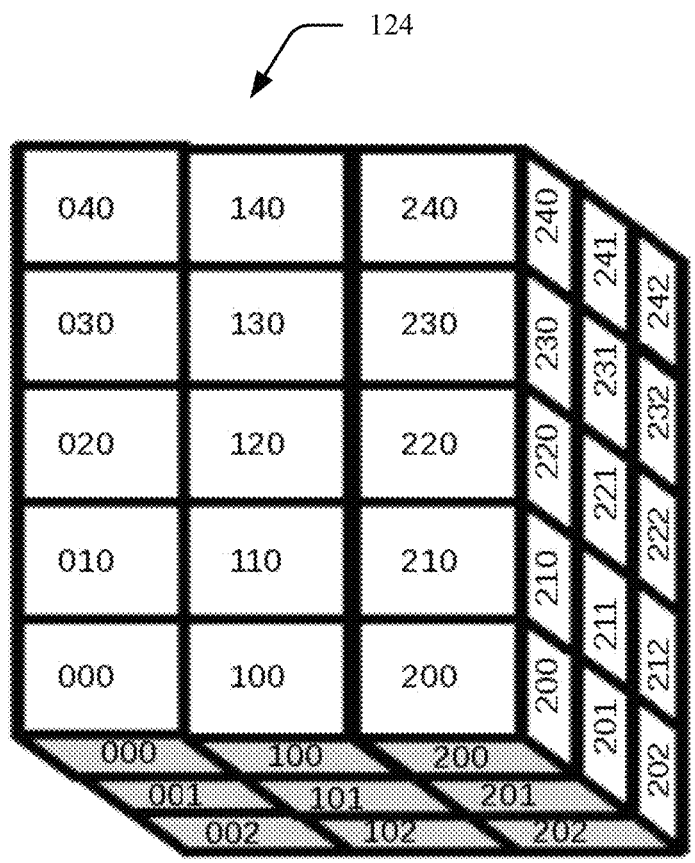
Figure 1:
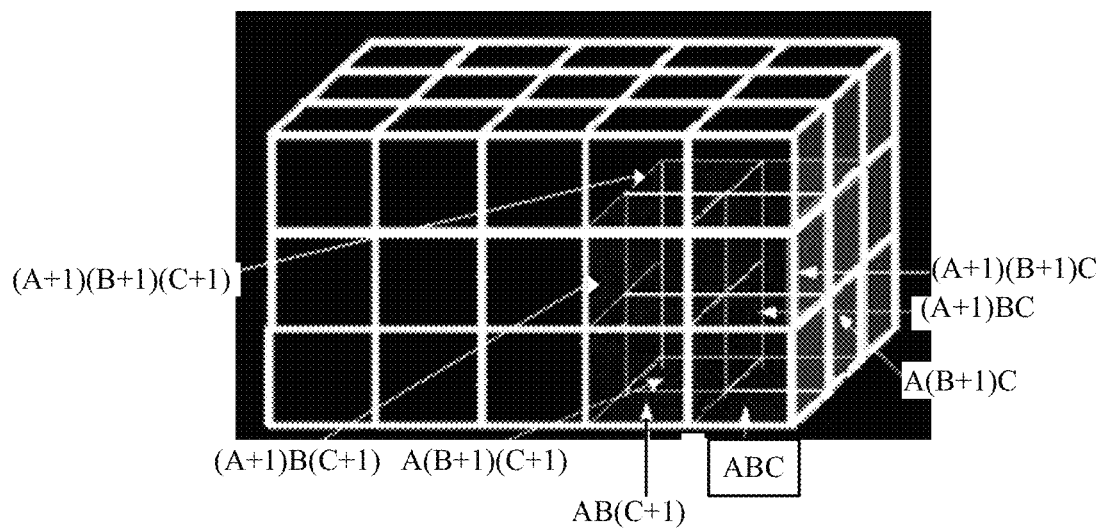

Systems and methods for assembly of metagenomic sequences are described herein. Generally, genetic material extracted directly from either a biological or an environmental sample, i.e., metagenome, is processed and stored as metagenomic data for research or medical purposes. The genetic material is sequenced to generate a plurality of nucleotide sequences, such as DNA or RNA sequences. The nucleotide sequences, also known as metagenomic sequences, may be subsequently assembled into genomic fragments, called contigs, corresponding to genomes of organisms residing in the environmental sample. The contigs may be further analyzed, for example, to estimate taxonomic diversity and the functional profiles of the organisms present in the environmental sample.

A variety of assembly techniques have been used for assembly of the metagenomic sequences derived from various organisms present in a given environmental sample into their corresponding contigs. Conventional assembly techniques involve comparing the metagenomic sequences with predetermined oligonucleotide frequency based models and tagging the metagenomic sequences to the models showing highest similarity. The metagenomic sequences tagged to similar models may then be assembled into contigs. However, metagenomic sequences belonging to unknown genomes may not show significant similarity to any of the models and may not be assembled into contigs, thus resulting in ambiguity and less efficient analysis.

Another conventional technique involves assembling the metagenomic sequences based on taxonomic origin of each of the metagenomic sequences. The metagenomic sequences having similar taxonomic origin may be assembled together to form contigs. However, the metagenomic sequences may not be efficiently assembled using the above approach, for example, when the metagenomic sequences belong to an organism that may not have been taxonomically classified. Metagenomic sequences belonging to such unknown organisms may thus not be assembled into the contigs, leading to ambiguous results and analysis of the metagenomic data.

Another conventional technique involves assembling the metagenomic sequences based on oligonucleotide usage patterns of the metagenomic sequences. According to the technique, the metagenomic sequences having similar oligonucleotide usage patterns may be initially grouped into clusters, using clustering techniques, such as K-means. Subsequently, metagenomic sequences belonging to a single cluster may be assembled into contigs. For the purpose, each of the metagenomic sequences is transformed into an n-dimensional vector, such that each of the n dimensions corresponds to the frequency of a specific oligonucleotide, of a given length, in the metagenomic sequences. Further, the metagenomic sequences may be grouped into clusters based on a relative difference obtained between their corresponding n-dimensional vectors. However, clustering the metagenomic sequences based on the frequencies of oligonucleotides of longer length may result in erroneous clustering, for example, in case of metagenomic sequences having lengths of less than 1000 bps. Further, assembling the metagenomic sequences belonging to such ambiguous clusters may result in incorrect contigs. Moreover, assembling the metagenomic sequences based on the frequencies may require increased time and computational resources, due to time required for computing the frequencies as well as distances between the n-dimensional vectors.

The present subject matter describes methods and systems for assembly of metagenomic sequences into contigs using an optimized method of data partitioning. Although the description herein is provided in considerable detail with respect to metagenomic data having metagenomic sequences corresponding to fragments of different genomes constituting the metagenomic data, it will be understood that the methods and systems for assembly can be implemented for genomic data having genomic fragments from the same genome as well, albeit with a few variations, as will be understood by a person skilled in the art. According to an embodiment of the present subject matter, metagenomic data having a plurality of metagenomic sequences is received for assembly into a plurality of contigs. As will be understood, each of the contigs constitutes metagenomic sequences corresponding to a distinct genome, with each genome being associated with a distinct organism residing in the environmental sample. Further, the contigs thus generated may be processed using a subsequent iteration of the above described process in order to obtain longer contigs or a complete genome corresponding to an organism residing in the environmental sample.

Each of the metagenomic sequences obtained from the metagenomic data is initially transformed into a 256 dimensional vector, hereinafter referred to as intermediate vectors, based on frequencies of all possible tetra-nucleotides for each of the metagenomic sequences. A plurality of intermediate vectors thus obtained are transformed into a plurality of sequence vectors in three dimensional space, such that each metagenomic sequence is represented as a sequence vector in the three dimensional space. In one implementation, the metagenomic sequences are represented as the sequence vectors using, for example, a set of reference points obtained based on a plurality of reference genomes. Further, based on the sequence vectors, a cuboid may be defined in the three dimensional space such that the cuboid encloses the sequence vectors corresponding to all the metagenomic sequences. Further, the cuboid may be divided into a plurality of equally sized smaller cuboids, hereinafter referred to as grids, such that each grid includes the sequence vectors and, in turn, the metagenomic sequences located within the coordinates defined by the particular grid in the cuboid.

Furthermore, each of the grids may be analyzed, using a method of progressive traversal, to identify and group all the metagenomic sequences which may belong to a particular genome. In one implementation, the grids are traversed such that, in each step of traversal, metagenomic sequences present in a grid and its neighboring grids, collectively referred to as a cluster of grids, are obtained. The metagenomic sequences thus obtained may be further assembled into contigs such that the metagenomic sequences having similar taxonomic origin are combined to form a single contig. Further, metagenomic sequences that have not been assembled during traversal of a particular grid, for example, due to absence of overlapping metagenomic sequences of similar taxonomic origin, may be considered for assembly during traversal of a subsequent grid. For example, the metagenomic sequences unassembled during traversal of a grid '000' may be considered for assembly along with metagenomic sequences obtained during traversal of the subsequent grid, i.e., a grid '100'. On traversal of all the grids, indexes of unassembled sequences and assembled sequences along with the contigs may be prepared and stored for further reference and/or analyses.

The present subject matter thus provides an efficient and easy method for assembly of metagenomic sequences into contigs using an optimized method of data partitioning. Partitioning the metagenomic sequences into the sequence vectors and the plurality of grids effectively reduces computational time required for analyzing and assembling the metagenomic sequences. Further, using the method of progressive traversal and assembling the metagenomic sequences of one cluster of grids at a time helps in optimizing resources required for an efficient assembly of the metagenomic sequences.

Although the description herein is with reference to metagenomic data, the systems and methods may be implemented for other data, such as genomic data, as well, albeit with a few variations, as will be understood by a person skilled in the art.

These and other advantages of the present subject matter would be described in greater detail in conjunction with the following figures. While aspects of described systems and methods for assembly of metagenomic sequence can be implemented in any number of different computing systems, environments, and/or configurations, the embodiments are described in the context of the following exemplary system(s).

FIG. 1(a) illustrates a metagenomic sequences assembly system 100, according to an implementation of the present subject matter. The metagenomic sequences assembly system 100 can be implemented in systems that include, but are not limited to, desktop computers, multiprocessor systems, laptops, network computers, cloud servers, minicomputers, mainframe computers, and the like. In one implementation, the metagenomic sequences assembly system 100, hereinafter referred to as, the system 100 includes interface(s) 102, one or more processor(s) 104, and a memory 106 coupled to the processor(s) 104.

The interfaces 102 may include a variety of software and hardware interfaces, for example, interfaces for peripheral device(s), such as a keyboard, a mouse, an external memory, and a printer. Further, the interfaces 102 may enable the system 100 to communicate with other devices, such as web servers and external databases. The interfaces 102 can facilitate multiple communications within a wide variety of networks and protocol types, including wired networks, for example, local area network (LAN), cable, etc., and wireless networks, such as Wireless LAN (WLAN), cellular, or satellite. For the purpose, the interfaces 102 may include one or more ports for connecting a number of computing systems with one another or to another server computer.

The processor(s) 104 can be a single processing unit or a number of units, all of which could include multiple computing units. The processor 104 may be implemented as one or more microprocessors, microcomputers, microcontrollers, digital signal processors, central processing units, state machines, logic circuitries, and/or any devices that manipulate signals based on operational instructions. Among other capabilities, the processor 104 is configured to fetch and execute computer-readable instructions and data stored in the memory 106.

The memory 106 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. The memory 106 also includes module(s) 108 and data 110.

The modules 108, amongst other things, include routines, programs, objects, components, data structures, etc., which perform particular tasks or implement particular abstract data types. The modules 108 further include a grid generation module 112, a sequence assembly module 114, and other module(s) 116. The other modules 116 may include programs that supplement applications on the system 100, for example, programs in the operating system. On the other hand, the data 110 serves, amongst other things, as a repository for storing data processed, received, and generated by one or more of the modules 108. The data 110 includes grid data 118, assembled data 120, and other data 122. The other data 122 includes data generated as a result of the execution of one or more modules in the modules 108.

In one implementation, the system 100 is associated with a metagenomic data repository (not shown in the figure). The metagenomic data repository, as will be understood, can be either external or internal to the system 100. The metagenomic data repository includes a plurality of metagenomic data files having metagenomic data generated by a metagenomic data generation platform, such as an NGS based platform. The metagenomic data, as will be understood, includes a plurality of metagenomic sequences corresponding to genomes of a plurality of organisms residing in the environmental sample. Although the description of the system 100 and the methods herein is provided in considerable detail with respect to metagenomic data having metagenomic sequences, it will be understood that the methods and systems for assembly can be implemented for genomic data having genomic fragments as well, albeit with a few variations, as will be understood by a person skilled in the art.

According to an embodiment of the present subject matter, metagenomic data having a plurality of metagenomic sequences is received by the system 100 for being assembled into a plurality of contigs. A contig may be understood as a group of metagenomic sequences corresponding to a distinct genome, with each genome being associated with a distinct organism residing in the environmental sample corresponding to the metagenomic data. In one implementation, the grid generation module 112 receives and stores the metagenomic data having the metagenomic sequences in the grid data 118. Further, the grid generation module 112 represents each of the metagenomic sequences in three dimensional space to obtain a plurality of sequence vectors. In one embodiment, the grid generation module 112 initially determines the frequencies of all possible tetra-nucleotides for each of the metagenomic sequences. Based on the determination, the grid generation module 112 represents the metagenomic sequences as 256 dimensional vectors. Thus, for each of the metagenomic sequences, the grid generation module 112 obtains a 256 dimensional vector, hereinafter referred to as intermediate vectors. Further, the grid generation module 112 may transform each of the intermediate vectors to the three dimensional sequence vectors.

In one embodiment, the grid generation module 112 obtains a sequence vector by computing a distance between the corresponding intermediate vector and a set of reference points. In one implementation, the grid generation module 112 obtains the set of reference points using a plurality of reference genomes retrieved from a reference database, for example, a database of all currently sequenced genomes. Further, the grid generation module 112 obtains the plurality of reference genomes such that each reference genome corresponds to a different genus. For example, the grid generation module 112 may retrieve reference genomes corresponding to 237 completely sequenced microbial genomes from a known genomic database, such as National Center for Biotechnology Information (NCBI) database.

The grid generation module 112 subsequently fragments each of the plurality of reference genomes into a plurality of non-overlapping reference fragments. For instance, in the previous example, the grid generation module 112 splits the 237 reference genomes into a plurality, say, 1000 base pairs of non-overlapping reference fragments. Further, the grid generation module 112 analyzes each of the reference fragments to compute a corresponding 256 dimensional fragment vector having frequencies of all possible tetra-nucleotides. Fragment vectors thus obtained are subsequently clustered into fragment clusters by the grid generation module 112 using any known clustering process. For instance, the grid generation module 112 may use K-means clustering approach for clustering of the fragment vectors to obtain the fragment clusters. In one implementation, the grid generation module 112 uses the K-means clustering approach to obtain k number of fragment clusters, wherein the value of k may be determined using the formula as given in equation 1.

$$k=\sqrt{n/2} \qquad (1)$$

where n is equal to the number of reference fragments obtained from the reference genomes.

Referring to the example discussed above, the grid generation module 112 may obtain a total of 631 fragment clusters using the reference fragments obtained from the 237 reference genomes. Further, the grid generation module 112 determines, for each of the fragment clusters, a cluster vector corresponding to the centroid of each fragment cluster. Based on the determination, the grid generation module 112 subsequently identifies three least correlated cluster vectors. In one implementation, the grid generation module 112 obtains a pairwise dot product between unit vectors corresponding to the cluster vectors and identifies a set of three cluster vectors having least pairwise dot product amongst them as the set of reference points. The grid generation module 112 thus identifies three cluster vectors as the reference points and stores the set of reference points in the grid data 118. It would be understood that the set of reference points thus generated represent nucleotide usage patterns observed in the known biological realm, thus ensuring a correct representation of the metagenomic sequences in the three dimensional space. Further, the reference points may be used by the grid generation module 112 to determine the sequence vectors corresponding to the metagenomic sequences, for example, by computing a distance between the corresponding intermediate vector and the set of reference points. The sequence vectors, as will be understood, help in determining Cartesian coordinates for the metagenomic sequences in three dimensional space.

Further, the grid generation module 112 defines a cuboid 124, as illustrated in FIG. 1(b), in the three dimensional space based on the sequence vectors. The cuboid 124 is generated such that it encompasses all the metagenomic sequences under consideration. For the purpose, the grid generation module 112 initially determines three dimensional coordinates, i.e., x, y, and z coordinates of each of the metagenomic sequences based on the sequence vectors. Further, the grid generation module 112 determines, for each of the x, y, and z directions of the three dimensional space, a farthest coordinate and a closest coordinate. The farthest coordinate in each direction may be defined as a maximum value in the corresponding direction among the three dimensional coordinates of the metagenomic sequences, i.e., the coordinate placed at a maximum distance from a point of origin in the three dimensional space. The closest coordinate in each direction may be defined as a minimum value from among the three dimensional coordinates of the metagenomic sequences, i.e., the coordinate placed at a least distance from the point of origin. The grid generation module 112 may subsequently define the cuboid 124 such that length of the cuboid 124 in each of the x, y, and z directions is equal to a difference between the farthest coordinate and the closest coordinate in the corresponding direction. Defining the boundaries of the cuboid 124 based on the farthest coordinate and the closest coordinate in each direction ensures that sequence vectors corresponding to all the metagenomic sequences are encompassed within the cuboid 124. The cuboid 124 thus obtained may be saved by the grid generation module 112 in the grid data 118.

Further, the grid generation module 112 may divide the cuboid 124 into a plurality of grids, as illustrated in the FIG. 1(b), such that each grid includes the sequence vectors, and in turn the metagenomic sequences, located within coordinates defined by the particular grid in the cuboid 124. In one implementation, the grids may be equally sized. Data related to the grids thus obtained may be stored by the grid generation module 112 in the grid data 118.

Based on the grids thus obtained, the sequence assembly module 114 may analyze the cuboid 124 to assemble the metagenomic sequences into contigs. In one implementation, the sequence assembly module 114 may use a method of progressive traversal to assemble the metagenomic sequences into contigs. Using the method of progressive traversal allows the sequence assembly module 114 to traverse the grids such that in each step of traversal, metagenomic sequences present in a grid under consideration and its neighboring grids, collectively referred to as a cluster of grids, are obtained. Initially, the sequence assembly module 114 identifies a grid, say, grid 'ABC', for analyses and traverses through the cluster of grids, formed by the grid 'ABC' and its immediate neighbors, in all three directions of the three dimensional space, as illustrated in the FIG. 1(c). In one implementation, the sequence assembly module 114 may traverse through the grid 'ABC' and seven immediate neighbors of the grid 'ABC', i.e., grids (A+1)BC, A(B+1)C, AB(C+1), (A+1)(B+1)C, A(B+1)(C+1), (A+1)B(C+1), (A+1)(B+1)(C+1), as illustrated in FIG. 1(c). Based on the traversal, the sequence assembly module 114 obtains a selective subset of metagenomic sequences, i.e., the metagenomic sequences encompassed by the cluster of grids for assembling into one or more contigs.

In one implementation, the sequence assembly module 114 may use any known method of sequence assembly, such as CAP3, SSAKE, SHARCGS, VCAKE, Newbler, Celera Assembler, AbySS, AllPaths, Velvet, Euler, and SOAPdenovo for assembling the selective subset of metagenomic sequences. Further, the sequence assembly module 114 assembles the selective metagenomic sequences into one or more contigs such that the metagenomic sequences originating from the same genome have a higher probability of getting combined to form a single contig. Thus, the above method of grid partitioning results in a high probability of metagenomic sequences originating from the same genome getting combined in to a single contig as the above method of grid partitioning helps in clustering the metagenomic sequences of similar origin together. The contigs thus obtained includes metagenomic sequences probably originating from the same genome, thus providing an efficient assembly of the metagenomic sequences. Additionally, the metagenomic sequences unassembled by the sequence assembly module 114 during a particular step of traversal, for example, due to absence of overlapping metagenomic sequences originating from the same genome may be considered for assembly during traversal of a subsequent grid. For instance, the sequence assembly module 114 may consider the metagenomic sequences unassembled during traversal of a grid '100' for assembly along with selective metagenomic sequences obtained during traversal of the subsequent grid, i.e., a grid '200'. The sequence assembly module 114 may thus traverse through all the grids and obtain a plurality of contigs. The plurality of contigs thus obtained by the sequence assembly module 114 is saved in the assembled data 120. In one implementation, the sequence assembly module 114 first performs the traversal in the X direction, followed by Y direction and finally in direction of the Z axis.

Further, the sequence assembly module 114 may combine the contigs, received after traversal of all the grids, into longer contigs or an entire genome. The contigs thus obtained may be saved in the assembled data 120. Further, the metagenomic sequences remaining unassembled after the traversal through the grids may also be saved in the assembled data 120. In addition, the sequence assembly module 114 may generate and store indexes of the unassembled metagenomic sequences and assembled metagenomic sequences along with the contigs in the assembled data 120 for further reference and/or analyses.

Validation and Results

For the purpose of validation, three distinct sets of simulated metagenomic data were downloaded from the online repository of simulated metagenomes present in the Fidelity of Analysis of Metagenomic Samples (FAMeS) database and assembled using the system 100 in accordance with the present embodiment. The results for assembly of the three distinct metagenomic data sets, i.e., simHC, simMC, and simLC were further compared with conventional techniques, such as CAP3. The simHC data sets are defined as data sets for which all constituting genomes are represented equally. The simMC data sets are defined as data sets in which a first half of the genomes have a high representation, where as remaining half of the genomes have a low representation. The simLC data sets are defined as data sets in which a few genomes are overrepresented as compared to other genomes.

Figure 2:
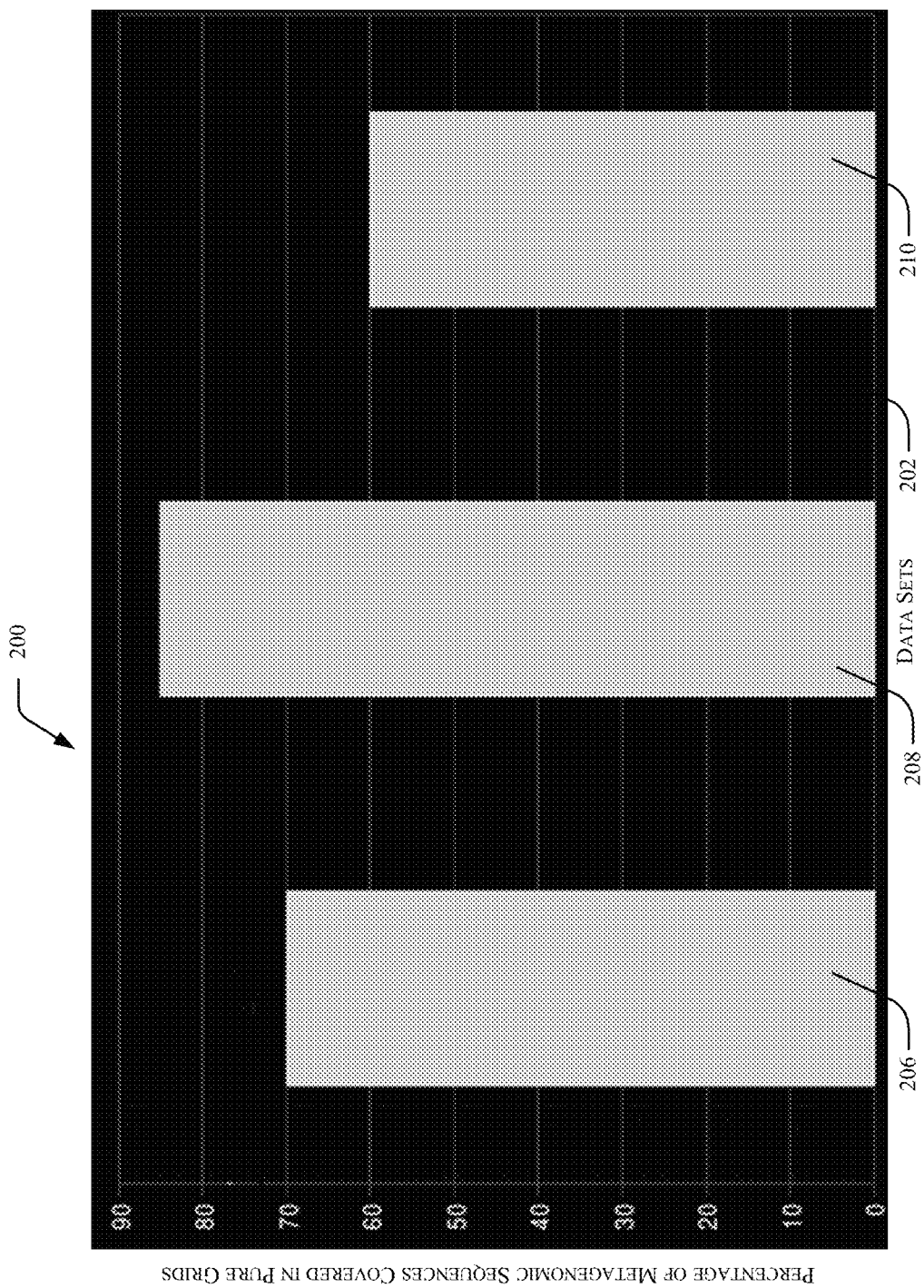
FIG. 2 illustrates a plot depicting percentage of metagenomic sequences covered in pure grids achieved using the metagenomic sequences assembly system, according to an embodiment of the present subject matter.

Further, the experiments were performed for two different validations. A first validation was performed for determining the resolving power of the metagenomic sequences assembly system to obtain grids containing taxonomically similar metagenomic sequences, which may facilitate their assembly into contigs. Initially the three distinct sets of metagenomes were provided as inputs to the system 100 and a cuboid, such as the cuboid 124 was defined based on the three distinct sets. The cuboid was further divided into a plurality of grids and analyzed to determine taxonomic affiliations of the metagenomic sequences covered in each grid. Based on the determination, purity of each grid was ascertained at phylum level of taxonomic classification. For this purpose, all grids having at least 70% of the metagenomic sequences belonging to a single phylum were ascertained as 'phylum-level-pure' grids. Results obtained after splitting the cuboid into grids using the system 100 are depicted in bar plot 200 illustrated in FIG. 2.

The plot 200 depicts percentage of metagenomic sequences covered in pure grids achieved for each data set using the system 100. In the plot 200, the three data sets used for validation are represented on a horizontal axis 202, while percentage of metagenomic sequences covered in pure grids obtained for the three data sets is represented on a vertical axis 204. In one implementation, purity level of grids obtained for the simLC data set are represented by a bar 206, for the simMC data set are represented by a bar 208, and for the simHC data set are represented by a bar 210. As illustrated in the plot 200, percentage of metagenomic sequences covered in pure grids was more than 60% for all the three data sets. Further, the percentage for the simLC and the simMC datasets was more than 70%. Such a high percentage of metagenomic sequences covered in the pure grids thus illustrates efficiency of the system 100 in pre-partitioning the metagenomic data for assembly.

Additionally, a second validation was performed for applicability of the grid assembly approach for assembly of metagenomic sequences. For the purpose, the three data sets were initially processed to obtain the plurality of grids and then assembled into contigs using the CAP3 assembly technique. Results thus obtained were compared with contigs obtained using only the CAP3 assembly technique. Results obtained after assembly of the metagenomic sequences using the system 100 and the conventional techniques were further analyzed based on three parameters, i.e., the average length of contigs, purity of the contigs, and number of metagenomic sequences assigned to the contigs as summarized in table 1.

TABLE 1

| Contig details | | System 100 | CAP3 |
|---|---|---|---|
| simHC | | | |
| 0 | 3000 | 8613 | 7023 |
| 3000 | 6000 | 17 | 13 |
| 6000 | 9000 | 0 | 0 |
| 9000 | 12000 | 0 | 0 |
| 12000 | 15000 | 0 | 0 |
| 15000 | 18000 | 0 | 0 |
| 18000 | 21000 | 0 | 0 |
| 21000 | 24000 | 0 | 0 |
| 24000 | 27000 | 0 | 0 |
| 27000 | 30000 | 0 | 0 |
| 30000 | 33000 | 0 | 0 |
| 33000 | 36000 | 0 | 0 |
| 36000 | 39000 | 0 | 0 |
| Total Number of contigs | | 8630 | 7036 |
| Average Length (bp) | | 1336 | 1347 |
| Percentage of Pure contigs | | 93.20% | 88.57% |
| Time taken in minutes | | 89 (184) | 75 |
| No. of sequences in contigs | | 19996 | 15694 |
| simMC | | | |
| 0 | 3000 | 10000 | 8677 |
| 3000 | 6000 | 873 | 694 |
| 6000 | 9000 | 52 | 44 |
| 9000 | 12000 | 4 | 6 |
| 12000 | 15000 | 1 | 0 |
| 15000 | 18000 | 0 | 0 |

TABLE 1-continued

| Contig details | | System 100 | CAP3 |
|---|---|---|---|
| 18000 | 21000 | 0 | 0 |
| 21000 | 24000 | 0 | 0 |
| 24000 | 27000 | 0 | 0 |
| 27000 | 30000 | 0 | 0 |
| 30000 | 33000 | 0 | 0 |
| 33000 | 36000 | 0 | 0 |
| 36000 | 39000 | 0 | 0 |
| Total Number of contigs | | 10930 | 9421 |
| Average Length (bp) | | 1782 | 1732 |
| Percentage of Pure contigs | | 98.31% | 96.79% |
| Time taken in minutes | | 145 (240) | 128 |
| No. of sequences in contigs | | 41734 | 36491 |
| simLC | | | |
| 0 | 3000 | 5881 | 6884 |
| 3000 | 6000 | 385 | 93 |
| 6000 | 9000 | 132 | 170 |
| 9000 | 12000 | 76 | 21 |
| 12000 | 15000 | 49 | 5 |
| 15000 | 18000 | 35 | 3 |
| 18000 | 21000 | 20 | 7 |
| 21000 | 24000 | 6 | 7 |
| 24000 | 27000 | 1 | 2 |
| 27000 | 30000 | 3 | 0 |
| 30000 | 33000 | 1 | 0 |
| 33000 | 36000 | 0 | 0 |
| 36000 | 39000 | 1 | 0 |
| Total Number of contigs | | 6590 | 7192 |
| Average Length (bp) | | 2088 | 1846 |
| Percentage of Pure contigs | | 98.37% | 95.72% |
| Time taken in minutes | | 152 (300) | 14 |
| No. of sequences in contigs | | 37793 | 37699 |

As illustrated in Table 1, percentage of pure contigs obtained using the system 100 was higher than the percentage achieved using the conventional technique for all the three data sets. Further, the contigs obtained using the system 100 constituted more number of metagenomic sequences as compared to the contigs obtained using the CAP3 technique thus indicating high efficiency in assembly of the metagenomic sequences. Additionally, average length of contigs obtained using the system 100 for the simMC and the simLC data sets were significantly longer than the average length achieved using the conventional technique. The system 100 may thus be efficiently used for generating contigs of higher length and purity.

Figure 3:
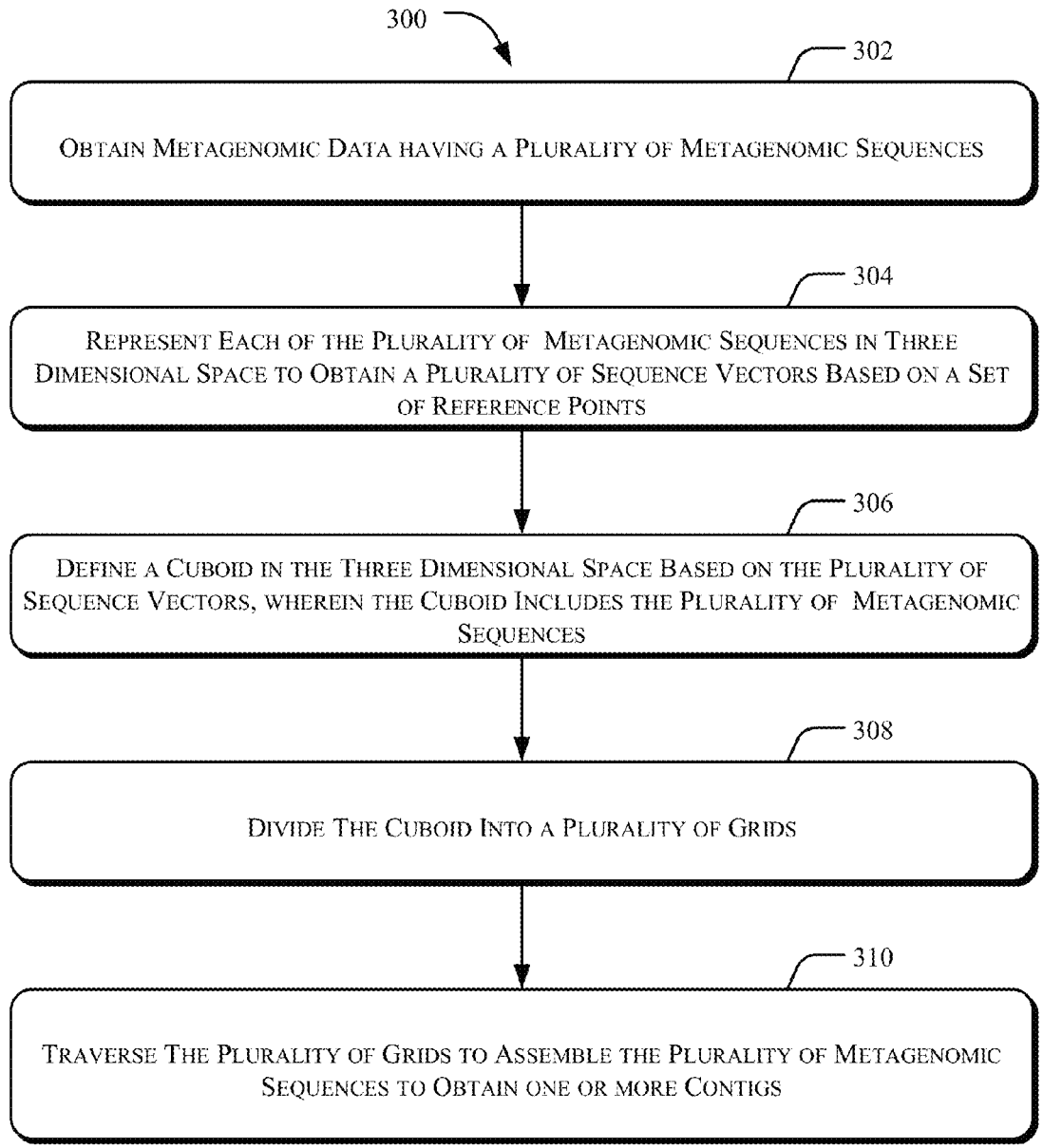
FIG. 3 illustrates a method for assembly of metagenomic sequences, in accordance with an embodiment of the present subject matter.
Figure 4:
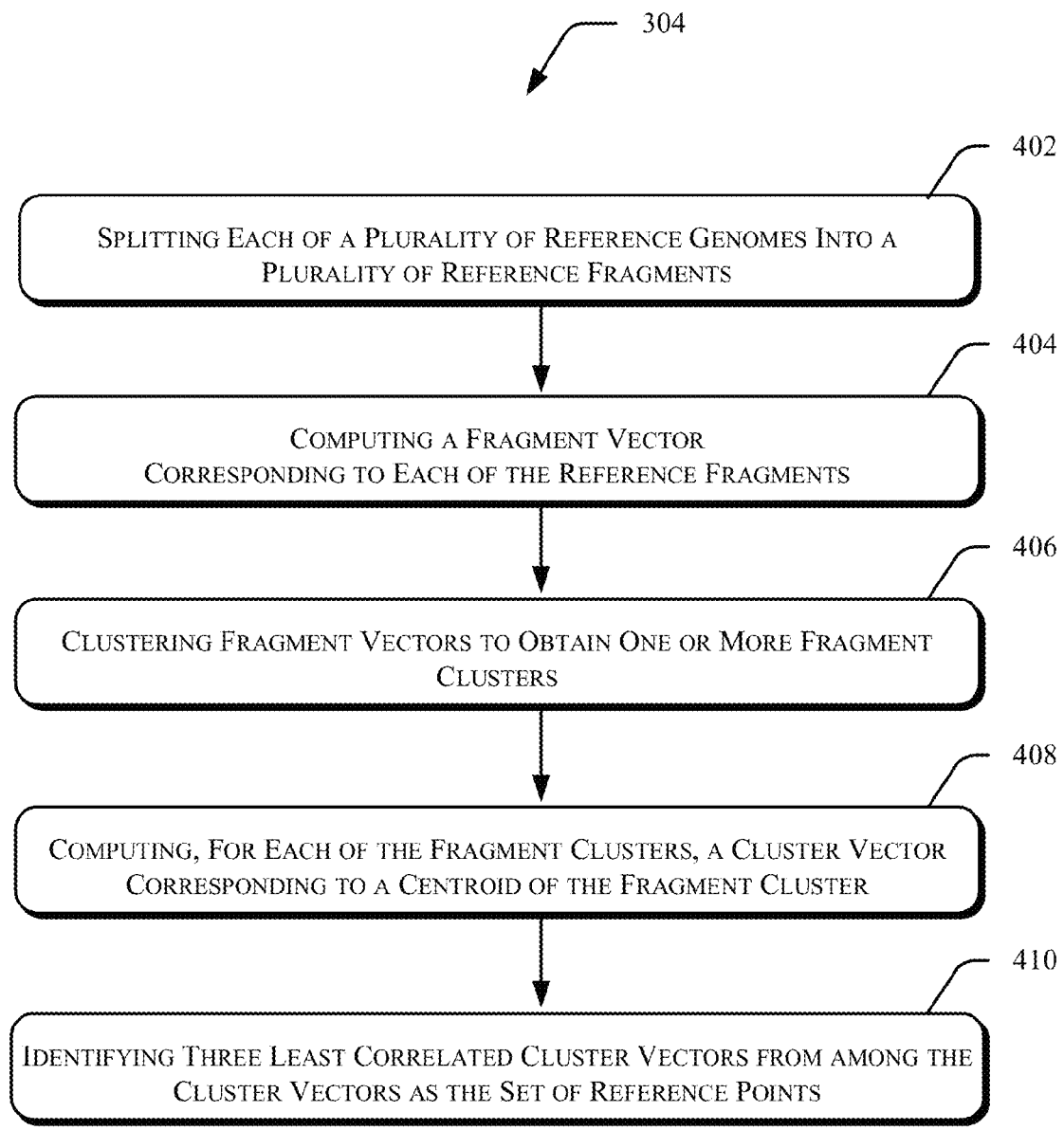
FIG. 4 illustrates a method of generating a set of reference points for assembly of the metagenomic sequences, in accordance with an embodiment of the present subject matter.

FIG. 3 illustrates a method 300 for assembly of metagenomic sequences, in accordance with an implementation of the present subject matter; FIG. 4 illustrates a method 304 for generating a set of reference points for assembly of the metagenomic sequences according to an embodiment of the present subject matter. The methods 300 and 304 are implemented in computing device, such as the metagenomic sequences assembly system 100.

The methods may be described in the general context of computer executable instructions. Generally, computer executable instructions can include routines, programs, objects, components, data structures, procedures, modules, functions, etc., that perform particular functions or implement particular abstract data types. The methods may also be practiced in a distributed computing environment where functions are performed by remote processing devices that are linked through a communications network.

The order in which the methods are described is not intended to be construed as a limitation, and some of the described method blocks can be combined in any order to implement the method, or an alternative method. Additionally, individual blocks may be deleted from the method without departing from the spirit and scope of the subject matter described herein. Furthermore, the methods can be implemented in any suitable hardware, software, firmware, or combination thereof.

At block 302, metagenomic data having a plurality of metagenomic sequences to be assembled is received, for example, by the system 100. In one implementation, the metagenomic data is obtained from a metagenomic data repository associated with the system 100. The metagenomic data includes a plurality of metagenomic sequences corresponding to genomes of a plurality of organisms residing in the environmental sample for which the metagenomic data is generated. In an implementation, the metagenomic data may be obtained by the grid generation module 112 and stored in the grid data 118.

At block 304, each of the plurality of metagenomic sequences is represented in three dimensional space to obtain a plurality of sequence vectors. In one implementation, a sequence vector is obtained for each of the metagenomic sequence by grid generation module 112 using, for example, a set of reference points such that a sequence is represented as a unique point in three dimensional space. Each sequence vector represents the corresponding metagenomic sequence in three dimensional space thus facilitating an easy and efficient partitioning of the metagenomic sequences for assembling into contigs. Further, the set of reference points used for transforming the metagenomic data sets may be obtained based on a plurality of reference fragments as will be described in greater detail with reference to FIG. 4.

At block 306, a cuboid is defined in the three dimensional space based on the plurality of sequence vectors, for example, by the grid generation module 112. In one implementation, the sequence vectors obtained for the metagenomic sequences are analyzed to determine a farthest coordinate and a closest coordinate for each of the x, y, and z axes of the three dimensional space. Based on the determination, length of the cuboid in each of the x, y, and z axes may be ascertained as a value equal to a difference between the farthest coordinate and the closest coordinate in the corresponding axis. Subsequently the cuboid may be defined in the three dimensional space such that it encompasses all the metagenomic sequences obtained for being assembled.

At block 308, the cuboid is divided into a plurality of smaller equally sized cuboids, hereinafter referred to as grids. In one implementation, the grid generation module 112 is configured to divide the cuboid into the plurality of grids such that each grid includes all the metagenomic sequences whose sequence vectors lie in the coordinates covered by the grid under consideration.

At block 310, the plurality of grids is progressively traversed to assemble the plurality of metagenomic sequences into one or more contigs. In one implementation, the plurality of grids may be traversed by a sequence assembly module, such as the sequence assembly module 114. The sequence assembly module 114 is configured to traverse the grids such that in each traversal, metagenomic sequences residing in the grid under consideration and its immediate neighbors are obtained and assembled into one or more contigs. Further, all the metagenomic sequences unassembled during a particular step of traversal are considered for assembly during a next step of traversal and so on till all the grids are traversed to obtain the contigs. The contigs may be further assembled into a plurality of longer contigs or complete genomes. The longer contigs or genomes thus obtained include metagenomic sequences probably originating from the same genome. Additionally, the contigs and the sequences remaining unassembled at the end of the traversal of the grids may be stored in the assembled data 120 of the system 100.

Referring to FIG. 4, the method 304 generates a set of reference points for representing the metagenomic sequences in the three dimensional space for assembling into contigs, according to an embodiment of the present subject matter.

At block 402, each of the plurality of reference genomes is split into a plurality of reference fragments. In one implementation, a plurality of reference genomes corresponding to distinct genera is obtained from a reference database, such as a database of all sequenced genomes. Further, each of the reference genomes are fragmented into the plurality of reference fragments, for example, by the grid generation module 112 and stored in the grid data 118.

At block 404, a plurality of fragment vectors corresponding to each of the reference fragments are computed, for example, by the grid generation module 112. In one implementation, each of the reference fragments are analyzed to compute a corresponding fragment vector having frequencies of all possible 256 tetra-nucleotides.

At block 406, fragment vectors obtained are clustered to obtain one or more fragment clusters, for example, by the grid generation module 112. In one implementation, the fragment vectors are clustered into one or more fragment clusters using any known clustering process, such as the K-means approach. For instance, the fragment vectors may be clustered into a total of 631 clusters using the K-means approach.

At block 408, a cluster vector corresponding to a centroid of each fragment cluster is computed. In one implementation, each of the fragment clusters are analyzed to ascertain a corresponding cluster vector. The computed cluster vectors may be further stored in the grid data 118.

At block 410, a set of reference points is obtained based on cluster vectors corresponding to the fragment clusters. The cluster vectors corresponding to the fragment clusters are analyzed, for example, by the grid generation module 112 to ascertain three least correlated cluster vectors as the set of reference points. In one implementation, the least correlated cluster vectors may be identified based on pairwise dot products computed for unit vectors corresponding to the cluster vectors. Further, the cluster vectors having least three pairwise dot products amongst them may be identified as the set of reference points. The set of reference points may be further used for representing the metagenomic sequences in the three dimensional space.

Although embodiments for assembly of metagenomic sequences have been described in language specific to structural features and/or methods, it is to be understood that the invention is not necessarily limited to the specific features or methods described. Rather, the specific features and methods are disclosed as exemplary embodiments for the assembly of metagenomic sequences.

We claim:

1. A computerized method for assembly of metagenomic sequences comprising:
   obtaining sequencing data of a plurality of organisms in an environmental sample to obtain a plurality of metagenomic sequences;
   for a metagenomic sequence of the plurality of metagenomic sequences, generating an intermediate vector which represents frequencies with which possible tetra-nucleotides occur in the metagenomic sequence;
   splitting the metagenomic sequence into fragments;
   for individual ones of the fragments, generating respective fragment vectors comprising the frequencies with which the possible tetra-nucleotides occur in the individual ones of the fragments;
   generating a plurality of fragment clusters by clustering the fragment vectors;

computing centroids of individual ones of the fragment clusters;

for individual ones of the centroids, generating respective cluster vectors;

identifying, as a set of reference points, three cluster vectors from the respective cluster vectors, the three cluster vectors having pairwise dot products which are the least correlated amongst computed pairwise dot products of combinations of individual ones of the respective cluster vectors;

transforming the intermediate vector into a three-dimensional sequence vector having coordinates determined by a distance between the intermediate vector and individual ones of the set of reference points, wherein the three-dimensional sequence vector corresponds to the metagenomic sequence;

defining a cuboid having a plurality of grids in a three-dimensional space encompassing the three-dimensional sequence vector, wherein individual ones of the plurality of grids encompass taxonomically similar metagenomic sequences from among the plurality of metagenomic sequences;

selecting a subset of the plurality of metagenomic sequences, wherein the subset includes a first metagenomic sequence located within coordinates defined by one of the plurality of grids in the cuboid and a second metagenomic sequence located within an immediate neighbor of the one of the plurality of grids in the cuboid; and assembling a one of the metagenomic sequences present in the subset with at least one other metagenomic sequence present in the subset into a contig, wherein the metagenomic sequence and the at least one other metagenomic sequence originate from a same genome.

2. The computerized method as claimed in claim 1, wherein defining the cuboid further comprises:

ascertaining three dimensional coordinates of the metagenomic sequences based on the three-dimensional sequence vector;

determining, for each axis of the three dimensional space, a farthest coordinate and a closest coordinate from among the three dimensional coordinates; and calculating a length of the cuboid in each axis based on a difference between the farthest coordinate and the closest coordinate in each axis.

3. A metagenomic sequences assembly system comprising:

a processor; and a memory coupled to the processor, the memory comprising:

a module configured to create a plurality of metagenomic sequences by obtaining sequencing data of a plurality of organisms in an environmental sample;

a grid generation module configured to:

determine, for a metagenomic sequence of the plurality of metagenomic sequences, frequencies with which possible tetra-nucleotides occur in the metagenomic sequence;

generate an intermediate vector which represents the frequencies;

split the metagenomic sequence into fragments;

generate respective fragment vectors comprising the frequencies with which the possible tetra-nucleotides occur in individual ones of the fragments;

cluster the fragment vectors to obtain one or more fragment clusters;

compute centroids for individual ones of the fragment clusters to obtain a plurality of cluster vectors corresponding to the respective centroids of the individual ones of the fragment clusters; and identify, as a set of reference points, three cluster vectors of the plurality of cluster vectors having pairwise dot products that are the least correlated amongst computed pairwise dot products of combinations of individual ones of the plurality of cluster vectors;

transform the intermediate vector into a three-dimensional sequence vector having coordinates determined by a distance between the intermediate vector and individual ones of the set of reference points, wherein the three-dimensional sequence vector corresponds to the metagenomic sequence;

define a cuboid in a three dimensional space, wherein the cuboid includes the metagenomic sequence corresponding to the three-dimensional sequence vector; and divide the cuboid into a plurality of grids, wherein a subset of the metagenomics sequences located within one of the plurality of grids encompass taxonomically similar metagenomic sequences from among the plurality of metagenomic sequences; and a sequence assembly module configured to:

select a subset of the plurality of metagenomic sequences, wherein the subset includes a first metagenomic sequence located within coordinates defined by one of the plurality of grids in the cuboid and a second metagenomic sequence located within an immediate neighbor of the one of the plurality of grids in the cuboid; and assemble a one of the metagenomic sequences present in the subset with at least one other metagenomic sequence present in the subset into a contig, wherein the one of the metagenomic sequences and the at least one other metagenomic sequence originate from a same genome.

4. The metagenomic sequences assembly system as claimed in claim 3, wherein the grid generation module is further configured to:

ascertain three dimensional coordinates of the metagenomic sequence based on the three-dimensional sequence vector;

determine, for each axis of the three dimensional space, a farthest coordinate and a closest coordinate from among the three dimensional coordinates; and calculate a length of the cuboid in each axis based on a difference between the farthest coordinate and the closest coordinate in each axis.

5. The metagenomic sequences assembly system as claimed in claim 3, wherein the sequence assembly module is further configured to:

ascertain, for one of the plurality of grids, an unassembled metagenomic sequence from among the subset of the plurality of metagenomic sequences; and cluster the unassembled metagenomic sequence with the one or more metagenomic sequences corresponding to a subsequent grid.

6. A non-transitory computer-readable medium having embodied thereon a computer program for executing a method comprising:

obtaining sequencing data of a plurality of organisms in an environmental sample to obtain a plurality of metagenomic sequences;

for a metagenomic sequence of the plurality of metagenomic sequences, generating an intermediate vector which represents frequencies with which possible tetra-nucleotides occur in the metagenomic sequence;

splitting the metagenomic sequence into fragments;

for individual ones of the fragments, generating respective fragment vectors comprising the frequencies with which the possible tetra-nucleotides occur in the individual ones of the fragments;

generating a plurality of fragment clusters by clustering the fragment vectors;

computing centroids of individual ones of the fragment clusters;

for individual ones of the centroids, generating respective cluster vectors;

identifying, as a set of reference points, three cluster vectors from the respective cluster vectors, the three cluster vectors having pairwise dot products that are the least correlated amongst computed pairwise dot products of combinations of individual ones of the respective cluster vectors;

transforming the intermediate vector into a three-dimensional sequence vector having coordinates determined by a distance between the intermediate vector and individual ones of the set of reference points, wherein the three-dimensional sequence vector corresponds to the metagenomic sequence;

defining a cuboid having a plurality of grids in a three-dimensional space encompassing the three-dimensional sequence vector, wherein individual ones of the plurality of grids encompass taxonomically similar metagenomic sequences from among the plurality of metagenomic sequences;

selecting a subset of the plurality of metagenomic sequences, wherein the subset includes a first metagenomic sequence located within coordinates defined by one of the plurality of grids in the cuboid and a second metagenomic sequence located within an immediate neighbor of the one of the plurality of grids in the cuboid; and assembling a one of the metagenomic sequences present in the subset with at least one other metagenomic sequence present in the subset into a contig, wherein the metagenomic sequence and the at least one other metagenomic sequence originate from a same genome.

7. The non-transitory computer-readable medium as claimed in claim 6, wherein defining the cuboid further comprises:

ascertaining three dimensional coordinates of the metagenomic sequences based on the three-dimensional sequence vector;

determining, for each axis of the three dimensional space, a farthest coordinate and a closest coordinate from among the three dimensional coordinates; and calculating a length of the cuboid in each axis based on a difference between the farthest coordinate and the closest coordinate in each axis.

\* \* \* \* \*